United States Patent [19]

Crosby et al.

[11] 4,145,360
[45] Mar. 20, 1979

[54] PRODUCTION OF ISOCYANATES

[75] Inventors: John Crosby; John A. Milner, both of Runcorn, England

[73] Assignee: Imperial Chemical Industries Limited, London, United Kingdom

[21] Appl. No.: 781,869

[22] Filed: Mar. 28, 1977

[30] Foreign Application Priority Data

Apr. 1, 1976 [GB] United Kingdom ............... 13302/76

[51] Int. Cl.$^2$ .................. C07C 118/00; C07D 273/00
[52] U.S. Cl. ........................... 260/453 P; 260/307 D; 260/307 F; 260/307 G; 260/453 A; 260/453 AP
[58] Field of Search ..................... 260/453 P

[56] References Cited

U.S. PATENT DOCUMENTS

| | | | |
|---|---|---|---|
| 3,560,518 | 2/1971 | Burk, Jr. et al. | 260/307 |
| 3,560,519 | 2/1971 | Burk, Jr. et al. | 260/307 |
| 3,609,162 | 9/1971 | Burk, Jr. et al. | 260/307 |
| 3,825,554 | 7/1974 | Burk, Jr. et al. | 260/307 A |
| 3,925,435 | 12/1975 | Crosby et al. | 260/453 P |
| 3,979,401 | 9/1976 | Burk, Jr. et al. | 260/301 |
| 4,029,686 | 6/1977 | Crosby et al. | 260/453 P |

FOREIGN PATENT DOCUMENTS

1620415 3/1970 Fed. Rep. of Germany.
1620416 3/1970 Fed. Rep. of Germany.

*Primary Examiner*—Dolph H. Torrence
*Attorney, Agent, or Firm*—Cushman, Darby & Cushman

[57] ABSTRACT

Process for the preparation of organic isocyanates in which a furoxan is heated in the presence of a vicinal diketo compound containing two adjacent keto carbonyl groups. When the furoxan ring is fused to an organic ring system di-isocyanates are produced. An adduct of the furoxan and the diketo compound may be isolated from the reaction mixture and used as a stable isocyanate precursor, for example, a "one-pot" polyurethane composition.

5 Claims, No Drawings

PRODUCTION OF ISOCYANATES

This invention relates to organic isocyanates and in particular to the production of novel precursors for organic isocyanates.

It is known that furoxans may be used to produce isocyanates by thermal decomposition but the reaction is not always easy to control.

We have now found that isocyanates may be satisfactorily produced from furoxans through the agency of novel intermediates which are precursors for the production of organic isocyanates. The precursors are adducts derived from furoxans and vicinal diketones which may be isolated from a mixture of these two compounds. We have found these adducts to be surprisingly useful for the production of isocyanates.

According to the present invention a process for the production of an organic isocyanate comprises heating a furoxan in the presence of a vicinal diketo compound containing two adjacent keto carbonyl groups.

A single furoxan ring will form two isocyanate groups and therefore this process is a convenient method for the production of diisocyanates i.e. compounds containing two isocyanate groups in the same molecule. For this purpose the furoxan should be a compound containing a furoxan ring fused to another organic ring system which will hold the two isocyanate groups together in the same molecule.

According to a preferred aspect of the present invention a process for the production of organic diisocyanates comprises heating a compound containing a furoxan ring fused to an organic ring system in the presence of a vicinal diketo compound containing two adjacent ketocarbonyl groups (hereinafter referred to as a vic-diketone) whereby an adduct of the two compounds is formed, the adduct subsequently being thermally decomposed to a diisocyanate.

The adduct of the furoxan and vic-diketone may usually be isolated, stored and used at a later time to make isocyanates. For this reason the adduct may be referred to as a precursor for the production of isocyanates.

According to another preferred aspect of the present invention a process is provided for the production of a precursor for organic diisocyanates comprising heating a compound containing a furoxan ring fused to an organic ring system in the presence of a vic-diketone and isolating the adduct formed thereby. In order to form a diisocyanate the adduct may be heated to a temperature higher than the highest temperature to which the furoxan and diketone were heated in order to form the adduct.

The temperature of formation of the adduct may be for example from ambient to 160° C. preferably from 50° C. to 100° C. The temperature of decomposition of the adduct to form isocyanate may be for example from 70° C. to 250° C. preferably from 120° C. to 200° C.

According to a further aspect of the present invention an adduct is provided of a vic-diketone and a furoxan compound containing a furoxan ring fused to an organic ring system comprising two molecules of the vic-diketone added to one molecule of the furoxan.

The adduct described above is believed to have a structure formed by the opening of the furoxan ring and the addition of one molecule of the vic diketo to each of the two nitrile oxide groups so formed.

The furoxan may be represented by the formula

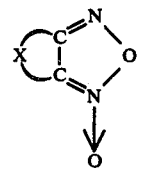

wherein X is an acyclic or cyclic divalent organic group which forms part of an organic ring system fused to the furoxan ring through the two carbon atoms shown.

The vic diketone may be represented by the formula

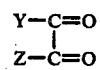

The adduct may be represented by the structure

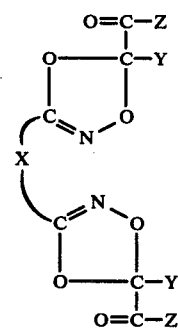

wherein X is a hereinbefore defined. Y, Z which may be the same or different are organic groups which are either separate or combined in one organic cyclic system. The adduct decomposes to a diisocyanate of formula

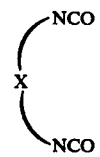

The organic group X which is part of the said organic ring system in the original furoxan may be acyclic alicyclic, aromatic or heterocyclic or a combination of two or more of any of these types. The group X should be more stable than the furoxan ring because in the process of the invention the furoxan ring is required to open but X is required to remain intact in order to retain both parts of the opened furoxan ring in the same molecule. Accordingly X is preferably a group thermally stable up to a temperature of 250° C. Groups which are wholly hydrocarbyl in structure are preferred and the most preferred are alicyclic groups especially when they are bridged and/or polycyclic in structure.

Substituents may be present in X provided they are inert substituents, not liable to take part in the reaction with the diketo compound. It is preferred that substituents by hydrocarbyl, chlorine or an ether group if the ring is substituted, but the most preferred structures for the group X are unsubstituted aliphatic ring systems including bridged and multi-ring systems possessing some ring-strain. The strain in the ring is believed in some way to contribute to the final reactivity of the isocyanate precursor.

In simplest form the ring system containing X in the furoxan may be a cyclopentane, cyclohexane or a benzpyran ring but more complex hydrocarbon ring systems are particularly suitable for example norbornane rings.

Examples of such furoxans include (a) "dicyclopentadiene" furoxan, (b) 3,4 propano furoxan, and (c) "camphor" furoxan,

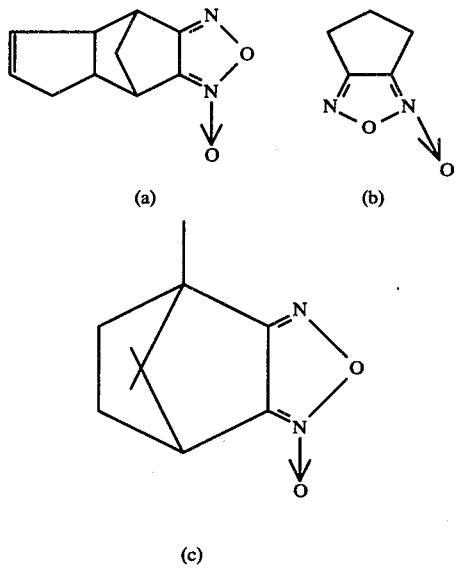

(a)    (b)

(c)

and furoxans having the following structural formulae:

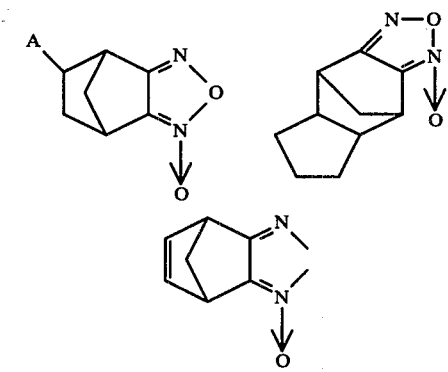

where A represents for example a hydrogen, alkyl, aryl or an alkyl carboxy group.

The vic diketone compound may be an aliphatic or aromatic compound having the vicinal ketone groups for example between aromatic nuclei, on an aliphatic chain portion of the molecule or on an alicyclic ring. It is desirable that the non-keto portions of the molecule (represented by Y and Z in formula above) do not compete with the reactivity of the keto groups towards either the furoxan rings or reactive intermediates derived therefrom. Accordingly if other groups or substituents are present they should be inert groups for example hydrocarbyl or halogen groups. We prefer to use compounds in which the sole functional group is the vicinal diketone group, the other parts of the molecule being hydrocarbon structures which provide a convenient framework for the operation of the diketone group on the furoxan.

Preferred diketone compounds include the following

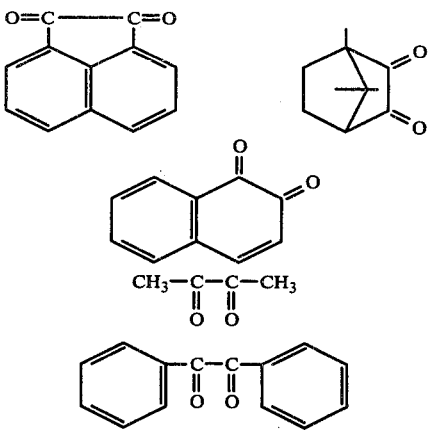

Suitable solvents, which include hydrocarbons, halogenated hydrocarbons, or ethers, should be inert to the reactants and products and have boiling points (under super-atmospheric pressure, if necessary) sufficiently high to enable the reactants to be maintained at the appropriate temperatures for the various processes involved. Examples of preferred solvents include toluene, xylene, dimethylformamide and dichlorobenzene. Preferably the solvent is chosen so that the reaction may be carried out at its reflux temperature.

It is convenient to choose a solvent with a b.pt. sufficiently different from that of the product isocyanate or its precursor to allow separation by simple distillation if appropriate.

The concentrations of furoxan and diketone dissolved in the solvent may be varied over a considerable range, depending on their solubility, but in general concentrations in the range 2 to 10% by weight are convenient.

The molar concentration of the diketone should be in excess and preferably approximately twice that of the furoxan.

The adduct which is the precursor for the isocyanate may be isolated and stored ready for use at a later time in the production of isocyanates. Alternatively the adduct may be converted to the isocyanate without isolation usually by raising the temperature of the solution above that at which the adduct is formed from the furoxan and di-ketone. If the adduct is isolated it may be used as a component of a so-called 'one-pot' composition for making polyurethanes. Accordingly the present invention includes the provision of a composition capable of producing a polyurethane by heating, comprising the adduct which is the subject of the present invention and an isocyanate-reactive precursor for a polyurethane preferably a compound having at least two hydroxyl groups, for example a glycol, polyol, polyetherglycol or polyester. The composition will form a polyurethane whenever subjected to conditions whereby the adduct will generate a diisocyanate, for example heating to a temperature in the range 150°–250° C. Diluents, extenders, catalysts, modifiers and antioxidants and the other additives and adjuvants well known in polyurethane technology may be added to the composition if desired. The advantage of this invention is that the adduct which is the isocyanate precursor may be added to the other reactants in the correct proportions and thus formulated as a complete package for use in the manufacture of a polyurethane, a package which would be stored ready for use requiring no further mixing or additional ingredients.

Furoxans for use as starting materials in the process of our invention may be made by any suitable route; but it may be convenient to prepare them by the addition of dinitrogen trioxide to a cyclic olefin to form the pseudonitrosite which can then be isomerised to the nitrooxime which may be cyclised with loss of water to give the furoxan. This latter method is described and exemplified in our earlier filed British patent specification No. 1,435,894 and German published OLS No. 2,336,403, the disclosure of which is incorporated herein by reference. Alternatively, for example, the furoxans may be prepared from the appropriate cyclic alkanone by the method of Ackrell et al. (*J C S Perkin I*, (1972), p. 1587)

Diisocyanate precursors prepared by the process of our invention will provide diisocyanates on heating and therefore may be used to form polyurethanes by reaction with suitable di or polyhydroxylic compounds. For example they may be reacted with bifunctional and/or trifunctional polyalkylene glycols or with other hydroxyl-ended polymers such as polyethylene tetramethylene adipate, to form polyurethanes. The reaction between isocyanate and hydroxylic compound may be readily carried out using known techniques for the manufacture of polyurethanes, in the presence of a suitable catalyst, for example dibutyl tin dilaurate. Similarly they may be reacted with suitable amino compounds to form ureas and with other materials commonly reacted with isocyanates.

The invention will be illustrated by the following Examples.

It will be appreciated that many of the products referred to in the Examples may exist in more than one isomeric form.

EXAMPLE 1

Preparation of Dicyclopentadiene Furoxan (DCPDF)

Step A:

Synthesis of dicyclopentadiene pseudonitrosite

A well stirred solution of dicyclopentadiene (66g) in n-pentane (1 liter), cooled in an ice bath, was treated with a mixed stream of nitric oxide (150 ml/min) and air (75–100 ml/min) for 3 hours. The mixture was purged with nitrogen and the solid product filtered off, sucked dry, washed with hot methanol and dried to give an almost colourless crystalline material, wt. 69g (66%) mp 122°–140° C., infra-red spectrum (Nujol mull) strong band at 1555 cm$^{-1}$.

Step B:

Synthesis of nitro oxime

The nitroso dimer from the previous preparation (20g) was heated at reflux under nitrogen in dioxane (500 ml) until the initial green colouration disappeared (40 minutes). Removal of the solvent afforded a yellow oil which slowly crystallised. Washing with methanol gave 7.5g of clean crystalline material with mp 135°–150° C.

Step C:

Synthesis of dicyclopentadiene furoxan

The nitro oxime from the previous preparation (2.20g) and 2.3g of a standardised DMF—SO$_3$ mixture (containing 5% excess SO$_3$ over the stoichiometric amount required for the dehydration reaction) were mixed; a further 1.5 ml of DMF was added to ensure the mixture was completely liquid at room temperature. The mixture was then set aside at room temperature in a stoppered flask for 65 hours.

The mixture was poured into water (60 ml) and extracted with dichloromethane (2 × 30 ml) to remove DMF. The acidic aqueous layer was then treated with 1N aqueous NaOH until the pH was approximately 8.5. The resulting emulsion of furoxan was extracted with CH$_2$Cl$_2$ (3 × 20 ml); the extracts were dried and evaporated to give crude furoxan as a pale yellow oil which crystallised on standing to give the crude product (2.05 g).

Crystallisation from ether-heptane afforded the pure furoxan as pale yellow crystals:

Yield 1.31g = 62%.

mp 98°–100° C.

I.R. 1655 cm$^{-1}$ (very strong) characteristic of furoxans C$_{10}$H$_{10}$N$_2$O$_2$ requires: 63.1%C, 5.26%H, 14.7%N; found: 63.1% C, 5.67%H, 14.6%N.

NB DCPDF may be handled safely in solution. However, when heated to 80°–85° C. on a gram scale, the solid decomposes explosively.

Preparation of adduct and decomposition to isocyanate

To a solution of dicyclopentadiene furoxan (1g) in toluene (30 ml), acenaphthaquinone (2g) was added. The solution was refluxed for 40 minutes. Evaporation under vacuum gave an oil which upon subjection to thin layer chromatography was shown to be a mixture of unreacted acenaphthaquinone and a major product of different composition. Pentane was added to the oil and crystallisation of the solution produced 1.96g of yellow crystals of the adduct, mpt 210°–213° C. Elemental analysis of the yellow crystals gave the following empirical formula C$_{17}$H$_{11}$NO$_3$.

|  | C | H | N |  |
|---|---|---|---|---|
| C$_{17}$H$_{11}$NO$_3$ requires: | 73.6 | 3.97 | 5.05 | % wt |
| found: | 73.56 | 4.18 | 4.87 | % wt |

The molecule formula of the compound was shown by mass spectrometry to be C$_{34}$H$_{22}$N$_2$O$_6$ corresponding to the structure

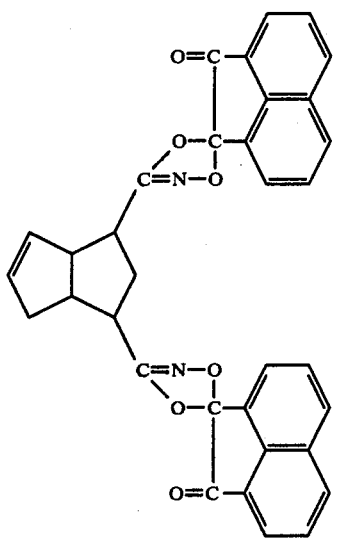

The adduct (1.77g) was dissolved in 50 ml of ortho-dichlorobenzene and heated under reflux for 50 minutes. On cooling to room temperature dark brown needles crystallised and were filtered off. The needles were washed with 10 ml cold O-dichlorobenzene to give 1.14g of a solid identical with acenaphthaquinone.

To the filtrate, which was shown to contain an isocyanate infra-red absorption band at 2260 cm$^{-1}$, was added 5 ml aniline. On standing at room temperature a precipitate was produced (0.51g) which was shown to be the urea:

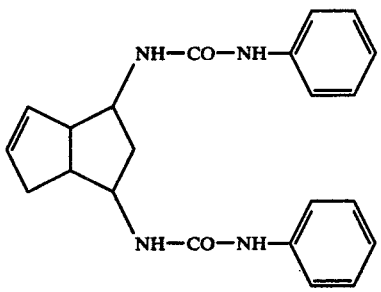

The structure of this compound was confirmed to be identical to that produced previously from the diisocyanate in our copending British Patent Application No. 53551/74 and characterised in Example 3 of that specification as that same structure.

I.R. peaks at 3320 & 3500 cm$^{-1}$ and 1640, 1600 & 1545 cm$^{-1}$.

|  | C | H | N |  |
| --- | --- | --- | --- | --- |
| Elemental Analysis Requires: | 70.2 | 6.39 | 14.9 | % wt |
| Found: | 68.1 | 6.27 | 14.55 | % wt |

EXAMPLE 2

Dicyclopentadiene furoxan (0.95g) in toluene (30 ml) was refluxed with dl camphor quinone (1.66g) for 30 minutes. Evaporation under vacuum gave a yellow oil which on trituration with a mixture of diethyl ether and cyclohexane gave a yellow solid (1.1g 62% yield) having a melting point of 133°–150° C.

The product (0.25g) was dissolved in O-dichlorobenzene (30 ml) and the solution was heated at reflux for 45 minutes. The presence of isocyanate in approximately the expected concentration was detected by infra-red spectroscopy.

EXAMPLE 3

Dicyclopentadiene furoxan (0.95g) was dissolved in toluene (30 ml) and to this solution was added or-thonaphthaquinone (1.58g). The solution was then heated under reflux for 45 minutes. Filtration and evaporation of the solution produced a solid of mpt 70° C. ± 5° C. Elemental analysis suggested that in addition to the main product containing 2 moles of quinone to each mole of furoxan an additional product was present containing a higher proportion of quinone.

Nevertheless the product was shown to behave as an isocyanate precursor. The product (0.25g) in O-dichlorobenzene (30 ml) was heated under reflux for 45 minutes whereupon the solution showed a large isocyanate infra-red absorption peak which previously was entirely absent.

EXAMPLE 4

Butane 2,3 dione (2 ml) was added to a solution of dicyclopentadiene furoxan (1.9g) in toluene (30 ml) and the solution was heated under reflux for 30 minutes. Evaporation under vacuum gave a yellow oil which was triturated with cold ether to give the adduct as a white solid (0.57g, 15.7% yield).

|  | C | H | N |  |
| --- | --- | --- | --- | --- |
| Found: | 59.33 | 6.08 | 7.74 | % wt |
| Required: | 59.67 | 6.08 | 7.73 | % wt |

The structure was confirmed by infra-red, nuclear magnetic resonance and mass spectrometry.

The product was refluxed in orthodichlorobenzene as in Example 4 and a quantitative yield of diisocyanate was produced. The diisocyanate was confirmed to be that expected having the molecular formula $C_8H_{10}(NCO)_2$ consistent with the original furoxan.

EXAMPLE 5

Dicyclopentadiene furoxan (1.52g) and benzil (3.4g) were heated under reflux in chlorobenzene (30 ml) for 45 minutes. The majority of the chlorobenzene was then removed by evaporation under reduced pressure to afford a brown oil, which on standing gave a crystalline buff-coloured solid (2.08g after washing with ether).

A small amount of the solid product was refluxed for five minutes in orthodichlorobenzene to give a solution which showed a large infra-red absorption band at 2260 cm$^{-1}$, indicative of isocyanate groups.

What we claim is:

1. A process for the production of an organic isocyanate comprising heating a furoxan having the formula:

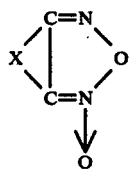

wherein X is an acyclic or cyclic divalent group which is free from substituents which are reactive with vicinal diketones in the presence of a molar excess of a vicinal diketo-compound having the formula:

wherein Y and Z are organic groups which are free of substitutents which are reactive with said furoxan.

2. A process for the production of an organic di-ioscyanate comprising the heating of a compound containing a furoxan ring fused to an organic ring system having the formula:

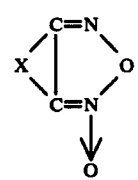

wherein X is a cyclic divalent group which is free from substituents which are reactive with vicinal diketones in the presence of a molar excess of a vicinal diketo-compound having the formula:

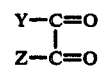

wherein X and Z are organic groups which are free of substituents which are reactive with said furoxan whereby an adduct of the two compounds is formed, and thermally decomposing the adduct to an organic di-isocyanate.

3. A process as claimed in claim 2 wherein the adduct is isolated and used subsequently to make the organic di-isocyanate.

4. A process as claimed in claim 1 wherein in order to produce the isocyanate the adduct is heated to a temperature higher than the highest temperature to which the furoxan and diketo-compounds were heated in order to form the adduct.

5. A process as claimed in claim 4 wherein the adduct is formed at a temperature in the range from ambient to 160° C. and decomposed at a temperature in the range from 70° to 250° C.

* * * * *